United States Patent [19]

Colon

[11] 4,334,081

[45] Jun. 8, 1982

[54] PREPARATION OF SUBSTITUTED OLEFINS

[75] Inventor: Ismael Colon, Middlesex, N.J.

[73] Assignee: Union Carbide Corporation, Danbury, Conn.

[21] Appl. No.: 227,931

[22] Filed: Jan. 23, 1981

[51] Int. Cl.³ .................... C07C 69/157; C07C 15/44; C07C 15/46; C07C 2/60
[52] U.S. Cl. .................................. 560/130; 585/438; 585/506; 585/514
[58] Field of Search ................ 560/130; 585/438, 506, 585/514

[56] References Cited

PUBLICATIONS

Odle, R. et al., *J. Org. Chem.*, vol. 45, 2709–2710, (1980).
Tamaru, Y. et al., *J. Org. Chem.*, vol. 43, 3396–3398, (1978).

*Primary Examiner*—Natalie Trousof
*Assistant Examiner*—Frederick W. Pepper
*Attorney, Agent, or Firm*—Bernard Francis Crowe

[57] ABSTRACT

Substituted olefins are prepared by the reaction of an organic halide with an olefin in the presence of a catalyst derived from zinc, a triarylphosphine and a nickel salt.

11 Claims, No Drawings

PREPARATION OF SUBSTITUTED OLEFINS

BACKGROUND OF THE INVENTION

This invention pertains to the preparation of substituted olefins and more particularly to the reaction of organic halides with olefins in the presence of a zinc-triarylphosphine-nickel salt catalyst.

The quest for substituted olefins is a continuing one because of the use of such compounds as monomers to produce homopolymers and copolymers. Styrene is a typical example of such a compound. The activity of the vinyl group also provides a host of versatile intermediates for further reactions including but not limited to halogenation, hydrogenation, nitration, sulfonation, cyanoalkylation, amination, and the like.

The general reaction of an organic iodide or bromide with an olefin is well established with palladium catalysts as demonstrated in the publications listed below.

J. E. Plevyak and R. F. Heck. *J. Org. Chem.*, 43, 2454, 1978;
R. F. Heck, *Acc. Chem. Res.*, 12, 146, 1979;
R. F. Heck, *Pure & Appl. Chem.*, 50, 691, 1978;
B. A. Patel, J. E. Dickerson and R. F. Heck, *J. Org. Chem.*, 43, 5018, 1978;
T. C. Zebovitz and R. F. Heck, *J. Org. Chem.*, 42, 3907, 1977;
H. A. Dieck and R. F. Heck, *J. Am. Chem. Soc.*, 96, 1133, 1974;
J. B. Melpolder and R. F. Heck, *J. Org. Chem.*, 41, 265, 1976;
B. A. Patel and R. F. Heck, *J. Org. Chem.*, 43, 3898, 1978;
J. E. Plevyak, J. E. Dickerson, and R. F. Heck, *J. Org. Chem.*, 44, 1979;
R. Odle, B. Blevins, M. Ratcliff and L. S. Hegedus, *J. Org. Chem.*, 45, 2709, 1980;
I. Arai and G. D. Daves, Jr., *J. Org. Chem.*, 44, 21, 1979;
Y. Tamaru, Y. Yamada and Z.-I. Yoshida, *J. Org. Chem.*, 43, 3396, 1978; and
Y. Tamaru, Y. Yamada and Z.-I. Yoshida, *Tet. Lett.*, 919, 1978.

With nickel systems one has greater reactivity and the use of organic chlorides becomes possible, but up till now the reaction has only been demonstrated by intramolecular olefin arylation as shown in the publications listed below.

R. G. Miller, D. R. Fahey, H. Golden and L. C. Satek, *J. Organomet. Chem.*, 82, 127, 1974;
D. R. Fahey and J. E. Mahan, *J. Molec. Catal.*, 3, 447, 1978;
M. Mori and Y. Ban, *Tet. Lett.*, 1803, 1976;
M. Mori and Y. Ban, *Tet. Lett.*, 1807, 1976;
M. Mori, S. Kudo and Y. Ban, *J. C. S. Perkin I*, 771, 1979; and
M. Mori and Y. Ban, *Tet. Lett.*, 1133, 1979.

SUMMARY OF THE INVENTION

A method of preparing substituted olefins has been found which comprises contacting organic halides free of nitro and acidic functional groups with an olefin which has 2 to about 18 carbons and is free of nitro substituents in an aprotic solvent system, optionally containing a mixture of polar and nonpolar solvents, with a catalytic amount of a catalyst mixture consisting essentially of:

(1) a nickel compound containing no radicals in which N and O are bonded directly together;
(2) a triarylphosphine having 6 to about 14 carbons in each aryl moiety, and
(3) zinc metal, at a temperature of about 25° C. to about 250° C.;

wherein the ratio of gram atoms of nickel per mole of organic halide is about 0.001 to about 1, the ratio of triarylphosphine to nickel is about 1 to about 100 moles per gram atom of nickel, and the amount of zinc in relation to that of nickel is about a 1 to 100 fold excess over that of the stoichiometric amount required to reduce all of the nickel present initially.

In the present invention, is disclosed a method for vinylic substitution with organic halides using a catalytic mixture of zinc, triarylphosphine, and nickel salt. An important feature of this invention is that it employs air stable reagents and can be conveniently performed by every bench chemist, since there is no need for exotic or expensive equipment. Another feature of this invention demonstrates that intermolecular reaction of an organic halide with ethylene or a monosubstituted olefin is feasible using nickel.

While the claimed method can be used at temperatures from 25° C. to 250° C., the preferred temperature range is from about 60° C. to 100° C. Although not essential, it is preferred to include a base, such as an amine, in the reaction mixture to minimize the amount of reduction which takes place due to the presumed formation of acid during the course of the reaction.

Exemplary bases include: triethylamine, tri-n-butylamine, pyridine, morpholine, pyrrolidine, and carbonates.

When ethylene or some other gaseous olefin is not used, then an inert atmosphere should be maintained over the reaction mixture.

Pressure is not critical, although when a gaseous olefin is used then one would expect that the rate of reaction would depend on the olefin pressure. As a matter of convenience, an atmosphere of the olefin gas is used, but the method is not limited to this pressure.

Suitable nickel salts are those reducible by zinc and other reducing metals such as magnesium. These compounds include nickel halides, nickel sulfates, nickel phosphates, nickel carbonates, nickel salts of organic acids, such as nickel formate, nickel acetate, and the like. It is also possible to use nickel organic complexes such as nickel acetylacetone, dichloro-bis(triphenylphosphine) nickel, bis(1,5-cyclooctadiene) nickel, tetrakis(triphenylphosphine) nickel, and the like.

Suitable triarylphosphines include triphenylphosphine, triphenylphosphines containing alkyl or alkoxy substituents having up to about eight carbon atoms, and unsubstituted or alkyl- and alkoxy-substituted trinaphthylphosphines.

Although other metals having a reduction potential suitable to reduce $Ni^{II}$ to $Ni^{I}$ or $Ni^{O}$ may be used, zinc metal is preferred. It is also preferred that the Zn metal be in finely divided form.

While the ratio of gram atoms of nickel per mole of organic halide can be about 0.001 to about 1, the preferred range is about 0.01 to about 0.1.

While the ratio of triarylphosphine to nickel can be about 1 to 100 moles per gram atom of nickel, the preferred range is about 3–30 moles per gram atom of nickel.

Although the actual substitution reaction should be catalytic in zinc, there are other side reactions which take place, such as coupling and reduction, which consume zinc. While an excess of zinc tends to promote these side reactions, it is necessary to have some excess zinc over that required to reduce all of the nickel$^{II}$ present initially. The preferred range of moles of zinc per gram atom of nickel is about 2-15.

Suitable aprotic solvents include: ethers, such as tetrahydrofuran (THF), 1,2-dimethoxyethane (DME), and diphenyl ether; aromatic hydrocarbons, such as, toluene, xylene and the like; and polar solvents, such as, ketones, amides, such as dimethyl formamide (DMF), sulfoxides and sulfones. Since nonpolar solvents tend to suppress coupling, while polar solvents promote formation of the active catalyst, it is preferred to form the active catalyst in a polar solvent and then add a nonpolar solvent prior to the addition of the reactants.

Suitable organic halides are those that undergo oxidative addition to $Ni^O$ reagents and do not contain nitro- or acidic functional groups. These comprise alkyl halides having 1 to about 20 carbons, aryl halides containing up to about 14 carbons, ethylenically unsaturated halogenated hydrocarbons having up to about 18 carbons, cycloaliphatic halides having up to about 14 carbons, and the like, and heterocyclic halides, such as halo thiophenes, halo furans, halo pyridines, and the like.

Preferred alkyl halides are: methyl chloride, methyl bromide, neopentyl chloride, benzyl chloride, and epichlorohydrin.

Preferred aryl halides are: chlorobenzene, p-chlorophenylacetate, p-chlorotoluene, p-chlorostyrene, and p-chlorostyrene oxide.

Preferred ethylenically unsaturated halogenated hydrocarbons are: vinyl chloride, vinyl bromide, 1-chloropropene, and 2-chloropropene.

Preferred cycloaliphatic halides are: chlorocyclopropane, chlorocyclopentane, chlorocyclohexane, and bromocyclohexane.

Suitable olefins are ethylene and monosubstituted α-olefins that do not contain nitro substituents and have up to about 18 carbon atoms. The olefins can be straight chain or branched. Exemplary olefins include: propylene, 1-butene, acrylonitrile, methyl acrylate, vinyl acetate, and styrene.

Dienes (conjugated and unconjugated) such as 1,3-butadiene, 1,4-pentadiene, and the like, as well as dienes where one of the unsaturated centers is monosubstituted, as in isoprene or neoprene, can also be used.

The invention is further described in the Examples which follow. All parts and percentages are by weight unless otherwise specified.

EXAMPLES 1-7

In examples 1-7 (Table I) the reactions were run in a two-neck flask equipped with a magnetic stirring bar. In each case the flask was charged with 0.13 g (1 mm) NiCl$_2$ and the specified amount of triphenylphosphine (TPP) and zinc dust. After sealing, the flask was evacuated and filled with nitrogen. Thirty ml of solvent were then introduced via syringe, and the mixture was stirred until the active red-brown catalyst was formed. The flask was then partially evacuated and an atmosphere of ethylene was introduced. If a base was used then it was normally introduced via syringe at this point, along with 2 ml of chlorobenzene. The mixture was then allowed to react for the specified time at the specified temperature, and the mixture was then analyzed by gas chromatography.

From the data in Table I, it can be noted that the styrene yield is affected most by temperature with the yield increasing with temperature. There does not appear to be a large effect upon changing the triphenylphosphine (TPP) concentration, but the amount of zinc has a significant effect on the amount of coupling (biphenyl) observed. With a large excess of zinc coupling becomes the major reaction. In addition to styrene, biphenyl, and unreacted chlorobenzene, benzene was observed in all cases but Example number 1. This product is believed to arise from reduction of chlorobenzene.

TABLE I

| Example | Solvent | TPP | Zn | Temp. | Reaction Time | Base$^A$ | Benzene | Styrene | Biphenyl |
|---|---|---|---|---|---|---|---|---|---|
| 1 | THF$^{(a)}$ | 2.0 g | 0.5 g | 40° C. | 24 hrs. | TEA | — | 2% | 0.5 |
| 2 | DMF$^{(b)}$ | 2.0 g | 0.5 g | 60° C. | 20 hrs. | TEA | 15.1 | 27.3% | 20.5 |
| 3 | DMF | 0.8 g | 2.0 g | 60° C. | 16 hrs. | TEA | 17.1 | 14.5% | 53.7 |
| 4 | DMF | 0.8 g | 2.0 g | 45° C. | 16 hrs. | TEA | 9.0 | 7.8% | 19.4 |
| 5 | DMF | 2.5 g | 2.0 g | 45° C. | 16 hrs. | TEA | 5.2 | 1.3% | 82.2 |
| 6 | DMAC$^{(c)}$ | 2.0 g | 0.5 g | 55° C. | 26 hrs. | — | 7.7 | 12.9% | 32.9 |
| 7 | DMAC | 1.3 g | 0.5 g | 45° C. | 20 hrs. | — | 2.3 | 4.1% | 10.7 |

$^A$TEA = triethylamine. One ml was used in Examples 1 and 2 and 2 mls were used in Examples 3-5.
$^{(a)}$Tetrahydrofuran.
$^{(b)}$Dimethylformamide.
$^{(c)}$Dimethylacetamide.

EXAMPLES 8-18

In examples 8-18 (Table II) the reactions were run at higher temperatures in mixed solvents. The use of fairly nonpolar solvents such as ethers and toluene was to minimize the amount of coupling. The reactions in examples 8-18 were run essentially in the same fashion as those in examples 1-7. The same amount of NiCl$_2$, and the specified amounts of zinc and triphenylphosphine were used. The catalyst was formed in 10 ml of dimethyl acetamide (DMAC) and then 20 ml of the nonpolar solvent were added. The reaction was then run in an identical fashion as in examples 1-7.

It was found that while the styrene formation was better at higher temperatures, there was a great deal of secondary reaction of the styrene produced at higher temperatures. In every case but example number 8, there was considerable secondary reaction. The conversion to styrene reported in Table II is the sum of the actual styrene yield plus the products of styrene secondary reaction. The seconcary products were stilbene, dimers of styrene (C$_{16}$H$_{16}$), and reduced dimers of styrene (C$_{16}$H$_{18}$) which were identified by mass spectrometry. Due to the secondary reactions, the yield of styrene under the conditions employed in these reactions did not exceed 20 percent.

It should be noted that under certain conditions, as in example 17, coupling could be reduced to almost insignificant levels, while even in the presence of a base, reduction (benzene formation) could not be significantly diminished.

TABLE II

| Example | Solvent | TPP | Zn | Temp. | Reaction Time | Base | Benzene | Styrene[A] | Biphenyl |
|---|---|---|---|---|---|---|---|---|---|
| 8 | Toluene | 2.4 g | 0.65 | 75° C. | 16 hrs. | — | 15.4 | 15.4 | 54.2 |
| 9 | Toluene | 2.4 g | 0.85 | 80° C. | 4 hrs. | Pyridine (2 ml) | 30.3 | 29.0 | 27.9 |
| 10 | Toluene | 2.6 g | 0.85 | 90° C. | 18 hrs. | — | 33.2 | 34.8 | 23.4 |
| 11 | Toluene | 1.6 g | 0.85 | 85° C. | 18 hrs. | $Na_2CO_3$ | 35.6 | 37.7 | 19.2 |
| 12 | Toluene | 2.4 g | 0.85 | 65° C. | 18 hrs. | — | 28.9 | 26.7 | 20.1 |
| 13 | Toluene | 2.4 g | 0.85 | 85° C. | 2 hrs. | Pyridine (2 ml) | 32.1 | 39.0 | 17.8 |
| 14 | Toluene | 2.4 g | 0.85 | 80° C. | 2½ hrs. | Pyridine (2 ml) | 34.3 | 38.8 | 12.7 |
| 15 | Toluene | 2.4 g | 0.85 | 80° C. | 6 hrs. | TEA (3.5 ml) | 38.2 | 28.8 | 7.4 |
| 16 | DME[B] | 2.4 g | 0.85 | 75° C. | 22 hrs. | TEA (3.5 ml) | 51.7 | 34.7 | 10.1 |
| 17 | Diphenylether | 2.4 g | 0.65 | 80° C. | 3 hrs. | Pyridine (2 ml) | 22.9 | 38.9 | 0.9 |
| 18 | Diphenylether | 2.4 g | 0.85 | 85° C. | 2½ hrs. | Pyridine (2 ml) | 34.2 | 38.2 | 9.6 |

[A] % conversion to styrene includes the amount of styrene plus secondary products due to styrene such as stilbene, dimers of styrene $C_{16}H_{16}$, and reduced dimers $C_{16}H_{18}$.
[B] DME = 1,2-dimethoxyethane.

EXAMPLE 19

In example number 19, chlorobenzene was replaced by 2.4 ml of p-chlorotoluene. Benzene was used as a nonpolar solvent, and 0.13 g $NiCl_2$, 2.4 g TPP, and 0.85 g of zinc were used. The reaction was run at 75° under an atmosphere of ethylene for four hours. After this period, gas chromatography analysis revealed that approximately 40 percent of the p-chlorotoluene had reacted, with 16.5 percent being converted to toluene, 10.7 percent to p-methylstyrene, and the bulk of the remainder due to secondary products of p-methylstyrene.

EXAMPLE 20

In example number 20, chlorobenzene was used to phenylate 1-decene. The catalyst was formed from 0.13 g $NiCl_2$, 2.0 g TPP, and 2.0 g Zn in 10 ml DMAC under an inert atmosphere. Twenty ml of toluene were then added, and several minutes later 1 ml of 1-decene and 2 ml of chlorobenzene were added. The reaction was run at 80° for 16 hours. After this period gas chromatography analysis revealed that virtually all of the chlorobenzene had reacted, but the major product was biphenyl (87 percent). Six percent of the chlorobenzene was converted to 1-phenyl-1-decene.

In all cases the styrene produced was either of polymerization grade or could be rendered so by a simple distillation in the presence of a free radical inhibitor, such as, hydroquinone or t-butyl catechol.

EXAMPLE 21

When Example 19 is repeated with the exception that the organic halide is p-chlorophenylacetate, p-acetoxystyrene is obtained. This upon hydrolysis affords p-hydroxystyrene.

Although the invention has been described in its preferred forms with a certain degree of particularity, it will be understood by those skilled in the art that the present disclosure has been made only by way of example and that numerous changes can be made without departing from the spirit and the scope of the invention.

What is claimed is:

1. A method of preparing substituted olefins which comprises reacting organic halides free of nitro and acidic functional groups with an olefin which has 2 to 18 carbons and is free of nitro substituents in an aprotic solvent system, optionally containing a mixture of polar and nonpolar solvents with a catalytic amount of a catalyst mixture consisting essentially of:
   (1) a nickel compound containing no radicals in which N and O are bonded directly together;
   (2) a triarylphosphine having 6 to about 14 carbons in each aryl moiety, and
   (3) zinc metal, at a temperature of up to about 250° C.;
wherein the ratio of gram atoms of nickel per mole of organic halide is about 0.001 to about 1, the ratio of triarylphosphine to nickel is about 1 to about 100 moles per gram atom of nickel and the amount of zinc in relation to that of nickel is about 1 to 100 fold excess over that of the stoichiometric amount required to reduce all of the nickel present initially.

2. Method claimed in claim 1 wherein the organic halide is an organic chloride.

3. Method claimed in claim 1 wherein about 2–15 moles of zinc are used per gram atom of nickel.

4. Method claimed in claim 1 wherein the organic halide is chlorobenzene and the olefin is ethylene.

5. Method claimed in claim 1 wherein the organic halide is p-chlorophenylacetate and the olefin is ethylene.

6. Method claimed in claim 1 wherein the reaction temperature is about 100° to about 160° C.

7. Method claimed in claim 1 wherein the triarylphosphine is triphenylphosphine.

8. Method claimed in claim 1 wherein the organic halide is p-chlorotoluene.

9. Method claimed in claim 1 wherein the aprotic solvent is dimethylformamide.

10. Method claimed in claim 1 wherein the solvent system contains the aprotic solvent dimethylacetamide and the non-polar solvent toluene.

11. Method claimed in claim 1 wherein the solvent system contains sufficient base to neutralize any acid formed during the preparation of the substituted olefin.

* * * * *